US012740693B2

(12) United States Patent
Martin

(10) Patent No.: US 12,740,693 B2
(45) Date of Patent: Sep. 22, 2026

(54) METHOD AND APPARATUS FOR ADJUSTING AND CONTROLLING PARAMETERS OF THE ILLUMINATION AREA OF OPHTHALMOLOGICAL DEVICES

(71) Applicant: Carl Zeiss Meditec AG, Jena (DE)

(72) Inventor: Dietrich Martin, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 523 days.

(21) Appl. No.: 18/006,502

(22) PCT Filed: Jul. 21, 2021

(86) PCT No.: PCT/EP2021/070317
§ 371 (c)(1),
(2) Date: Jan. 23, 2023

(87) PCT Pub. No.: WO2022/018108
PCT Pub. Date: Jan. 27, 2022

(65) Prior Publication Data

US 2023/0284889 A1 Sep. 14, 2023

(30) Foreign Application Priority Data

Jul. 24, 2020 (DE) ......................... 102020209379.2

(51) Int. Cl.
*A61B 3/12* (2006.01)
*A61B 1/06* (2006.01)
(Continued)

(52) U.S. Cl.
CPC .......... *A61B 1/0655* (2022.02); *A61B 3/0008* (2013.01); *A61B 3/135* (2013.01)

(58) Field of Classification Search
CPC ......... A61B 3/02; A61B 3/102; A61B 3/1025; A61B 3/113; A61B 3/1015; A61B 3/108;
(Continued)

(56) References Cited

U.S. PATENT DOCUMENTS 8,488,895 B2 7/2013 Muller et al.
2003/0053031 A1 3/2003 Wirth
(Continued)

FOREIGN PATENT DOCUMENTS

CN 110036328 7/2019
DE 10128650 3/2004
(Continued)

OTHER PUBLICATIONS

International Search Report (English Translation) and Written Opinion for PCT/EP2021/070317 date mailed Nov. 17, 2021.
(Continued)

*Primary Examiner* — Dawayne Pinkney
(74) *Attorney, Agent, or Firm* — DeWitt LLP

(57) ABSTRACT

A method and device for adjusting and controlling parameters of the illumination area of ophthalmological devices including for example, brightness, color/color temperature, area shape, polarization state. The arrangement according to the invention includes an actuating unit that adjusts the desired lighting parameters, an illumination unit that generates illumination radiation having the desired illumination parameters, a decoupling element that decouples a part of the illumination radiation, a sensor element that analyzes the decoupled part of the illumination radiation and an evaluation unit that evaluates the sensor data and that determines the actual illumination parameters of the illumination radiation. According to an example embodiment of the invention, the sensor element is a spatially resolving image sensor. Embodiments of the invention are provided in particular for adjusting and controlling parameters of the illumination area of ophthalmological devices, but can also be applied to other technical fields, such as microscopy, for example.

18 Claims, 2 Drawing Sheets

(51) Int. Cl.

| | |
|---|---|
| ***A61B 3/00*** | (2006.01) |
| ***A61B 3/02*** | (2006.01) |
| ***A61B 3/10*** | (2006.01) |
| *A61B 3/135* | (2006.01) |

(58) Field of Classification Search

CPC ..... A61B 3/0083; A61B 3/1225; A61B 3/024; A61B 3/005

USPC ................ 351/201, 205, 206, 209–211, 218, 351/221–223, 245, 246

See application file for complete search history.

(56) References Cited

U.S. PATENT DOCUMENTS

| | | | | |
|---|---|---|---|---|
| 2006/0268231 | A1 | 11/2006 | Gil et al. | |
| 2009/0207874 | A1 * | 8/2009 | Zimare | A61F 9/008 372/108 |
| 2011/0080421 | A1 * | 4/2011 | Capener | G09G 5/10 345/589 |
| 2011/0176110 | A1 | 7/2011 | Bublitz et al. | |
| 2013/0138094 | A1 * | 5/2013 | Fabrikant | A61F 9/00804 606/5 |
| 2013/0301004 | A1 | 11/2013 | Kahn et al. | |
| 2014/0139807 | A1 | 5/2014 | Uchiyama | |
| 2018/0239220 | A1 * | 8/2018 | Peraelae | H04N 23/74 |
| 2020/0390325 | A1 | 12/2020 | Pascal et al. | |

FOREIGN PATENT DOCUMENTS

| | | |
|---|---|---|
| DE | 102004046375 | 4/2006 |
| WO | WO2013081619 | 6/2013 |
| WO | WO2015003274 | 1/2015 |

OTHER PUBLICATIONS

European Office Action for EP Application No. 21754929.4 dated Feb. 24, 2026.

Notification of the First Office Action (English translation provided) and Search Report for Chinese Patent Application No. 202180059702.5 dated Jun. 12, 2025.

* cited by examiner

METHOD AND APPARATUS FOR ADJUSTING AND CONTROLLING PARAMETERS OF THE ILLUMINATION AREA OF OPHTHALMOLOGICAL DEVICES

RELATED APPLICATIONS

This application claims priority from Application PCT/EP2021/070317, filed Jul. 21, 2021, and claims priority from DE Patent Application No. 10 2020 209 379.2 filed Jul. 24, 2020, each of which are incorporated by reference in their entireties in this application.

TECHNICAL FIELD OF THE INVENTION

The present invention relates to a method and an apparatus for adjusting and controlling parameters of the illumination field of ophthalmological devices. By way of example, brightness, color/color temperature, field shape, state of polarization or the like can be considered to be parameters in this context.

BACKGROUND

Parameters of the illumination field in laser-based applications are generally controlled by analyzing an output coupled, defined portion of the radiation.

The shape of the wavefront in optical systems is monitored in similar fashion according to the known prior art. A defined, small portion of the radiation to be monitored is output coupled, recorded by a dedicated sensor (e.g., a Shack-Hartmann sensor) and evaluated. In this case, too, the information obtained is used to influence the wavefront in a targeted manner.

In contrast thereto, parameters of the illumination field of ophthalmological devices, such as slit lamps, fundus cameras or the like, have hitherto not been set at all, not been set completely or only been set indirectly via scales to be calibrated on the operating elements.

There is no control of the light distribution occurring in the real illumination field with regard to brightness or color, or else the position, width and height of a slit or the like.

Since the position of the operating elements is usually defined according to ergonomic aspects, the said operating elements often are not in the direct vicinity of the assemblies to be influenced. However, the paths for transferring the operating settings can be susceptible to errors, and so, especially after the device has been used for a relatively long period of time, it is not possible to rule out that there will be discrepancies between the scale setting and the light distribution properties generated as a result.

In order to allow repeated adjustments of operating elements, some ophthalmological devices comprise scales without units, as a result of which approximately the same settings can be applied reproducibly at least at different points in time. The disadvantage here, however, is that the settings are made on the operating elements without really knowing which corresponding parameters of the illumination field are really set therewith.

In modern ophthalmological devices, it is becoming increasingly important to have information about the real parameters used in the illumination field also available in electronic form, for example in order to allow the documentation thereof and/or the use thereof in a control loop. Moreover, the availability of this information in electronic form allows it to be made available to the user in the eyepiece or on a display.

This can significantly improve their workflow as they can maintain their position vis-a-vis the device and have all the relevant information available.

Furthermore, the electronic availability of such parameter information opens up the possibility of using this as (meta) information in automated further processes such as image processing, deep learning or other artificial intelligence methods.

The availability of the really used parameters of the illumination field in electronic form is of particular importance, especially with regard to the aspect of remotely controlled use of ophthalmological diagnostic devices (also known under the term telemedicine). In this context, the external operator is fully dependent on reliable feedback regarding the current device configuration and, in particular, also the real parameters of the illumination field.

In this respect, WO 2013/081619 A1 describes a system for ophthalmological-imaging. Example embodiments of the invention are based on an ophthalmological apparatus that is controlled via a network and records stereoscopic or three-dimensional images. In so doing, the system can be accessed remotely by one or more physicians to dynamically control every aspect of an ophthalomological device in real time over the network and to verbally interact with the patient. The recorded three-dimensional images of the patient's eyes are transmitted in real time to the physician, who can thus perform an eye examination of at least one portion of an eye. Since the ophthalmological device is controlled over a network in real time, the physician can vary and refine the images in order to optimize the examination. Using the system present, comprehensive eye exams can be performed remotely with as much detail and clarity as if the physician were present at the same location as the patient.

Both the importance and the desire to use such device parameters in order to be able to generate an advantage or added value for the user can be gathered from various citations in the prior art.

Known solutions describe the use of a wide variety of illumination parameters in order to make these available to the user as an aid for the operation of ophthalmological devices.

By way of example, using a slit lamp microscope, the eye is illuminated with a slit aperture in order to carry out a magnified observation of all anterior segment structures of the eye, the cornea, the sclera, the iris, the crystalline lens, the conjunctiva, the eye chamber, the corner angle, the vitreous humor and the retina. Moreover, there are various observation techniques that use slit lamp microscopes. These include different illumination and image recording methods. By way of example, the illumination can be implemented diffusely, directly and tangentially or else as background illumination. As imaging methods, fluorescent staining photography or photography using a gonioscope or a fixing lens are widely used. It should be noted that observation targets and observation techniques are combined and applied as desired within the scope of examinations using a slit lamp microscope.

For slit lamp microscope examinations, it is necessary, depending on the selection of the observation target and/or observation technique, to accordingly adapt the settings of the optical system, for example irradiation angle, amount of illumination light, observation magnification, slit width, filter, and also of the image recording system, such as light sensitivity, shutter speed, aperture value, etc. Only then are optimal image recordings and examinations possible with little stress on the physician and patient.

However, it is difficult to appropriately implement or change the settings of the optical system and imaging system in accordance with the various combinations of observation targets and/or observation techniques. In particular, such problems arise when the physician has little experience of using a slit lamp microscope for examination purposes.

In this respect, US 2014/0139807 A1 describes a slit lamp microscope with which the setting of the optical system can be easily adapted to the different conditions.

To this end, the slit lamp microscope has a storage unit configured to store correspondence information which links default setting conditions of illumination and/or observation systems to each of a plurality of sites of an eye. Default setting conditions are, for example: the value of the observation magnification, the slit width, the amount of light, the irradiation angle, the presence or absence of irradiation of the background illumination light, and the presence or absence of a diffusion element, a stop or a filter in the light path.

After defining the site of the eye to be examined, the default setting conditions for that site are searched in the correspondence information and are compared to the current setting states detected previously, and the setting states differing from the searched default setting conditions are found. The differing setting states are then output on a display unit in order to be able to be corrected accordingly. However, the described solution seems to be more about the use of the data in the form of the default setting conditions, because the extraction of the data is only indicated very vaguely.

According to the known prior art, such data are obtained with the aid of various sensors. In this case, axially coupled potentiometers are used particularly frequently for the detection of rotary or translatory movements. Other possible sensors are based on detecting changes in the properties of resonant circuits, capacitances, the Hall effect or the like.

The required dynamic and value ranges for such sensors represent a particular challenge. In the case of a slit lamp microscope, for example, it is necessary to determine the slit width with an accuracy of better than 25 μm if slit widths between 100 μm and 20 mm are intended to be set.

The mechanical change in position of diffusion elements, stops or filters needs be determined in order to detect the presence or absence thereof in the light path, but this is often very difficult given the cramped installation space.

For reasons of space, it may occasionally also be necessary for sensors not to be arranged directly on the component influencing the illuminated field parameters, but rather be arranged along the control chain somewhere between the actuator (e.g., rotary knob, sliding element, . . . ) and the component. This leads to systematic and random deviations, hysteresis and other errors that can only be partially compensated for by calibration processes.

A disadvantage of the known systems is also that different sensors, including signal and supply lines and evaluation electronics, are required to determine the very different parameters of the illumination field.

In addition to solving installation space problems, it is also necessary to ensure that the various transducers and/or sensors do not influence one another or that the change in one of the transducers is really only detected by the associated sensor.

The latter becomes particularly problematic if, for example in the case of a slit lamp microscope, some assemblies with a number of parameters to be set, and thus also with a plurality of transducers, sensors, connection lines and the like, have to be moved relative to the housing.

SUMMARY OF THE INVENTION

Example embodiments of the invention overcome many of the disadvantages of the solutions known from the prior art and present a solution for setting and controlling a multiplicity of parameters of the illumination and/or observation field of ophthalmological devices, which solution makes do with as few sensors as possible and in the process minimizes the susceptibility of the said sensors to faults and mutual interference.

In an example method for setting and controlling parameters of the illumination field of ophthalmological devices, in which the desired illumination parameters are set, an illumination radiation with the desired illumination parameters is generated and converted into a light distribution in the focal plane, a portion of the illumination radiation is output coupled and directed to a sensor element for analysis, and the real illumination parameters of the illumination radiation are determined from the sensor data a spatially resolving image sensor is used as the sensor element for analyzing the output coupled portion of the illumination radiation.

Possible spatially resolving image sensors can be based on CMOS or CCD technology, for example, but other technologies are also conceivable in the future.

In accordance with a first example embodiment, the output coupled portion of the radiation reflects the real light distribution and does not change the latter as far as possible. The image sensor of the digital camera records image data continuously or sequentially, utilizing the dynamic range of the image sensor.

According to a second example embodiment, the image data recorded by the image sensor are checked for their validity in a first step.

Calibration values are used to determine the parameters from the recorded image data. Furthermore, the ascertained, real illumination parameters are made available to the user or to software available to them as a numerical and/or pictorial representation and are presented on a display or in an observation beam path.

Although the proposed example embodiments are intended in particular for setting and controlling parameters of the illumination field of ophthalmological devices, they can also be used in other technical fields, such as microscopy, for example.

BRIEF DESCRIPTION OF THE DRAWINGS

The invention is described in more detail below on the basis of example embodiments. In this respect.

DETAILED DESCRIPTION

Figure 1:
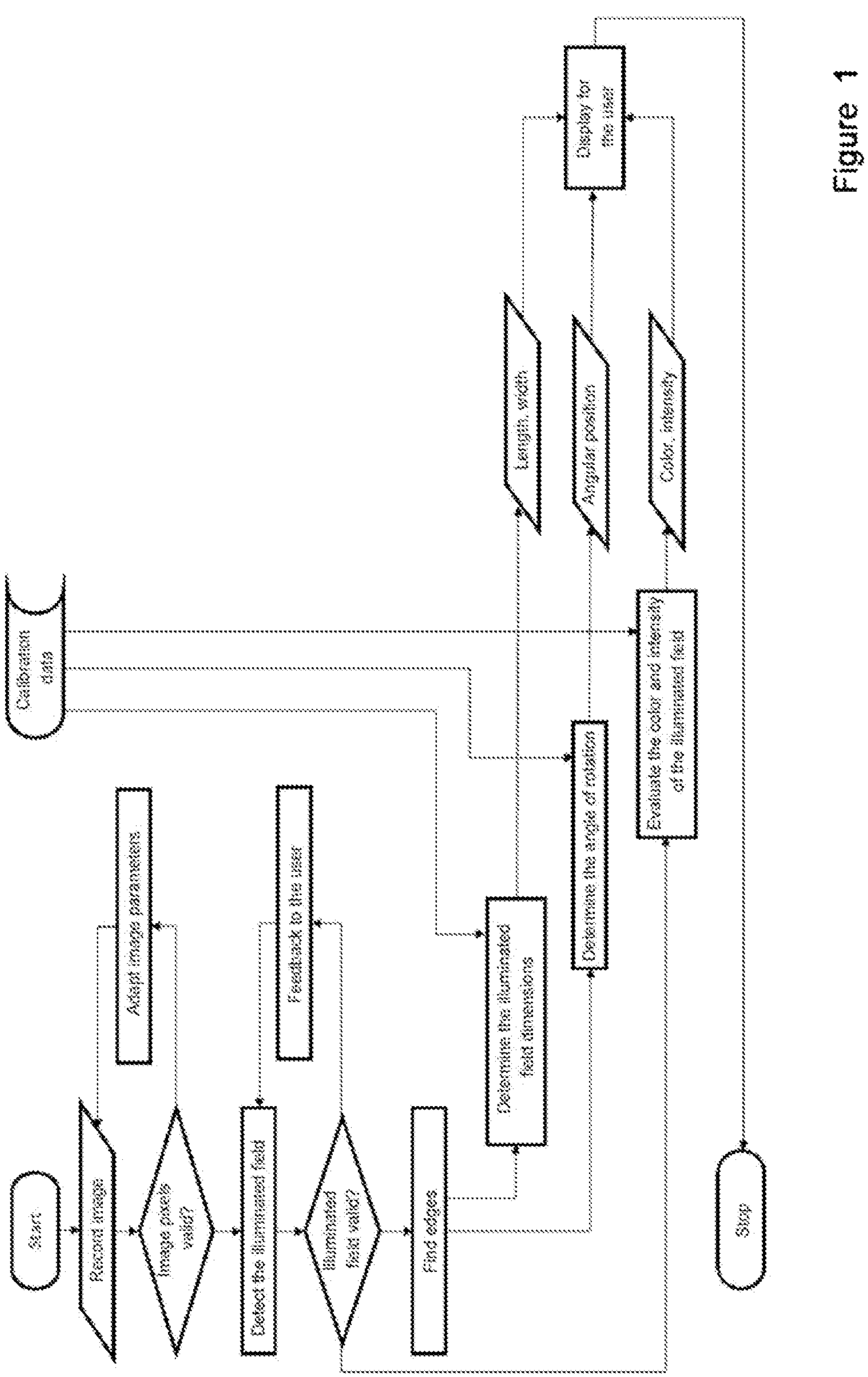
FIG. 1: is a schematic representation of the course of the method according to the invention in the form of a flowchart

In the example method for setting and controlling parameters of the illumination field of ophthalmological devices, the desired illumination parameters are set, an illumination radiation with the desired illumination parameters is generated and converted into a light distribution in the focal plane, a portion of the illumination radiation is output coupled and directed to a sensor element for analysis purposes, and the real illumination parameters of the illumination radiation are determined from the sensor data. According to embodiments of the invention, a spatially resolving image sensor is used as the sensor element for analyzing the output coupled portion of the illumination radiation. In this case, the geometric resolution of the sensor can be adapted to the accuracy required by the application. As a result, it is also possible to use very cost-effective sensors for a lower sensor resolution, for example sensors comparable to those of optical mice (computer input devices).

The spatially resolving image sensor of a camera is for example used.

In this case, the illumination parameters are specified by the system or the user in the form of information and are set in such a way that a desired light distribution is generated in a/the focal plane.

According to example embodiments, the following illumination parameters, for example, are used to generate a desired light distribution: brightness, color, light field shape, polarization and the like.

In this case, the brightness of a light distribution can be set and optionally corrected by changing the current or voltage at the light source(s) and the light color or color temperature can be set and optionally corrected with the aid of filters or by combining different colored light sources and their targeted amplification or weakening.

While the field shape of the light distribution can be changed by stops, DMD, ELCoS, or the like, polarizers are required to change its polarization.

What is essential to the invention is that the output coupled portion of the radiation actually reflects the real light distribution and does not change the latter as far as possible as a result of the output coupling.

Should the output coupled beam be changed, this must be taken into account when determining the real illumination parameters of the illumination radiation. To do this, however, the influence of this change must be known. This can be determined, for example, during the manufacturing process in the form of a calibration, the specific parameters can be stored in the module and thus be kept available for further use.

In accordance with an example embodiment of the method according to the invention, image data are recorded continuously or sequentially by the spatially resolving image sensor. In this case, the dynamic range of the image sensor can be utilized for example and used as a light output detector. To this end, particular attention is paid to ensuring that the individual pixels are not overdriven or that the dynamic range of the camera used is utilized. To this end, the pixels with the highest intensity are selected and camera parameters, for example exposure time or gain, are set via an algorithm (e.g., a binary search) so that these pixels assume a value just below the upper dynamic range.

As a result, there should no longer be any overdriven or underdriven pixels in the entire image and all of the data can be used for further analysis. In this case, these camera settings can also be subsequently used as parameters.

The image data recorded by the spatially resolving image sensor are analyzed and the parameters are determined therefrom using adapted and/or optimized algorithms. In a first step, the recorded image data can be checked for their validity.

To this end, the image data are examined using an algorithm in order to determine whether there are one or more illuminated fields in the camera images. Only a single illuminated field is expected. Should a plurality thereof be found, it is possible that the system has not been set optimally. Then the subsequent algorithm steps are not necessarily valid either. Ideally, the user should be informed of this.

The image data recorded by the spatially resolving image sensor are subsequently used to determine the parameters using adapted and/or optimized algorithms.

To determine the parameters, use is made of calibration values, which, for example, compare the size, angle and color representation once between the image field and the analyzed result of the image sensor.

To determine the width, length and orientation of the slit, the illuminated field and its edges are detected with the aid of an algorithm from the image data recorded by the image sensor. In this case, the distance between the two parallel edges corresponds to the slit width and the perpendicular distance to the slit height. The center line between the two detected edges represents the reference to the angle-of-rotation evaluation of the slit position.

The color of the illuminated field can be inferred from the intensity of the differently colored partial images of the image data recorded by the image sensor.

Since only a small selection of filters are generally used in ophthalmological devices, the assignment of the sensor-detected light distribution to the filter in use is not too much of a problem. The corresponding filter-dependent histograms of the light distribution can be stored in the sensor within the scope of the adjustment/calibration process.

After image processing algorithms have been used to determine whether one or more of the desired parameters are set correctly, the ascertained real illumination parameters of the illumination radiation are stored for documentation and/or reproduction purposes.

In particular, the parameters determined from the recorded images and their size can be stored as meta information for the recorded image or used as an input variable for a control loop of the illumination module.

In accordance with a further example embodiment of the method according to the invention, the real illumination parameters are made available to the user as numerical and/or pictorial representation.

This is implemented, for example, on a display or directly in the observation beam path.

In this respect, FIG. 1 shows a possible course of the method according to the invention in the form of a flowchart.

After the desired illumination parameters have been set and an illumination radiation with the corresponding illumination parameters has been generated, a portion of the generated light distribution is output coupled and analyzed, and the real illumination parameters of the illumination radiation are determined therefrom.

To this end, an image is recorded by the spatially resolving image sensor, checked for validity and repeated in the absence of validity, with the image recording parameters being able to be adjusted where necessary. The illuminated field is detected from the valid image data, likewise checked for validity and repeated in the absence thereof, with the user being able to receive feedback about this.

In a first step, the edges of the slit image representation are detected from the valid illuminated fields, their dimensions are determined and for example displayed for the user. Calibration data can additionally be used to this end.

In a second step, the angle of rotation of the slit image representation is determined and for example likewise displayed to the user. In this context, the center line between the two detected long edges represents the reference for evaluating the angle of rotation. Calibration data can additionally also be used to this end.

In a third step, the intensity is determined and the color of the illuminated field is deduced from the intensity of differently colored partial images.

At the same time, after a corresponding calibration, the intensity of the light source can be deduced from the measured intensity for a given exposure time of the camera.

The proposed arrangement for setting and controlling parameters of the illumination field of ophthalmological devices includes of an actuating unit for setting the desired illumination parameters, an illumination unit for generating an illumination radiation with the desired illumination parameters, an output coupling element for output coupling a portion of the illumination radiation, a sensor element for analyzing the output coupled portion of the Illumination radiation, and an evaluation unit for evaluating the sensor data and determining the real illumination parameters of the illumination radiation. According to the invention, the sensor element for analyzing the output coupled portion of the illumination radiation is a spatially resolving image sensor which can record both intensities and information in a spatially resolved manner.

In accordance with a first example embodiment of the arrangement according to the invention, the sensor element is the spatially resolving image sensor of a camera.

In order to be able to evaluate color information, the image sensor must have spectrally differently reacting parts. The BAYER matrix filter present in many cameras, for example, is also suitable to this end.

In accordance with an example embodiment of the arrangement according to the invention, the illumination unit consists of a plurality of spectrally different and separately controllable light sources. The illumination unit moreover has a variable stop to increase the dynamic range.

As already described above, the following illumination parameters, for example, are used to generate a desired light distribution: brightness, color, light field shape, polarization and the like. In this case, the brightness of a light distribution can be set and optionally corrected by changing the current or voltage at the light source(s) and the light color or color temperature can be set and optionally corrected with the aid of filters or by combining different colored light sources and their targeted amplification or weakening. The field shape of the light distribution can be changed by stops, DMD, ELCoS, or the like.

In order to be able to determine the parameters of the real light distribution, a portion of the radiation which actually reflects the real light distribution is output coupled. The beam splitter provided to this end transmits this portion of the radiation for analysis purposes to the spatially resolving image sensor serving as the sensor element.

However, the output coupling element for output coupling a portion of the illumination radiation can also be an already existing element in the form of a mirror or prism, with an optically effective surface being designed as a partially transparent layer rather than a reflective optical layer.

As already described, the spatially resolving image sensor is designed to record image data continuously or sequentially and transmit the said image data to the evaluation unit for the evaluation thereof and for the determination of the real illumination parameters of the illumination radiation.

The evaluation unit comprises a microprocessor for analyzing the images recorded by the image sensor and for determining the real illumination parameters of the illumination radiation.

The microprocessor analyzes the recorded image data by using adapted/optimized algorithms and determines the parameters and their size. To this end, calibration values are for example used which, for example, compare the size, angle and color representation once between the set, desired illumination parameters and the image data which were recorded by the image sensor and which characterize the real light distribution in the focal plane.

The arrangement according to the invention can comprise a storage unit for documenting and/or reproducing the real illumination parameters of the illumination radiation. In this case, the ascertained real illumination parameters of the illumination radiation can be stored as input variables of a control loop for the illumination unit, or else as meta information for the recorded image data.

In particular, this can be brought to the attention of the user. To this end, the arrangement can comprise an element for numerical and/or pictorial representation of the real illumination parameters.

The numerical and/or pictorial representation can be implemented on a display or directly in the observation beam path, for the purposes of which the arrangement comprises an element for input coupling into an observation beam path.

Figure 2:
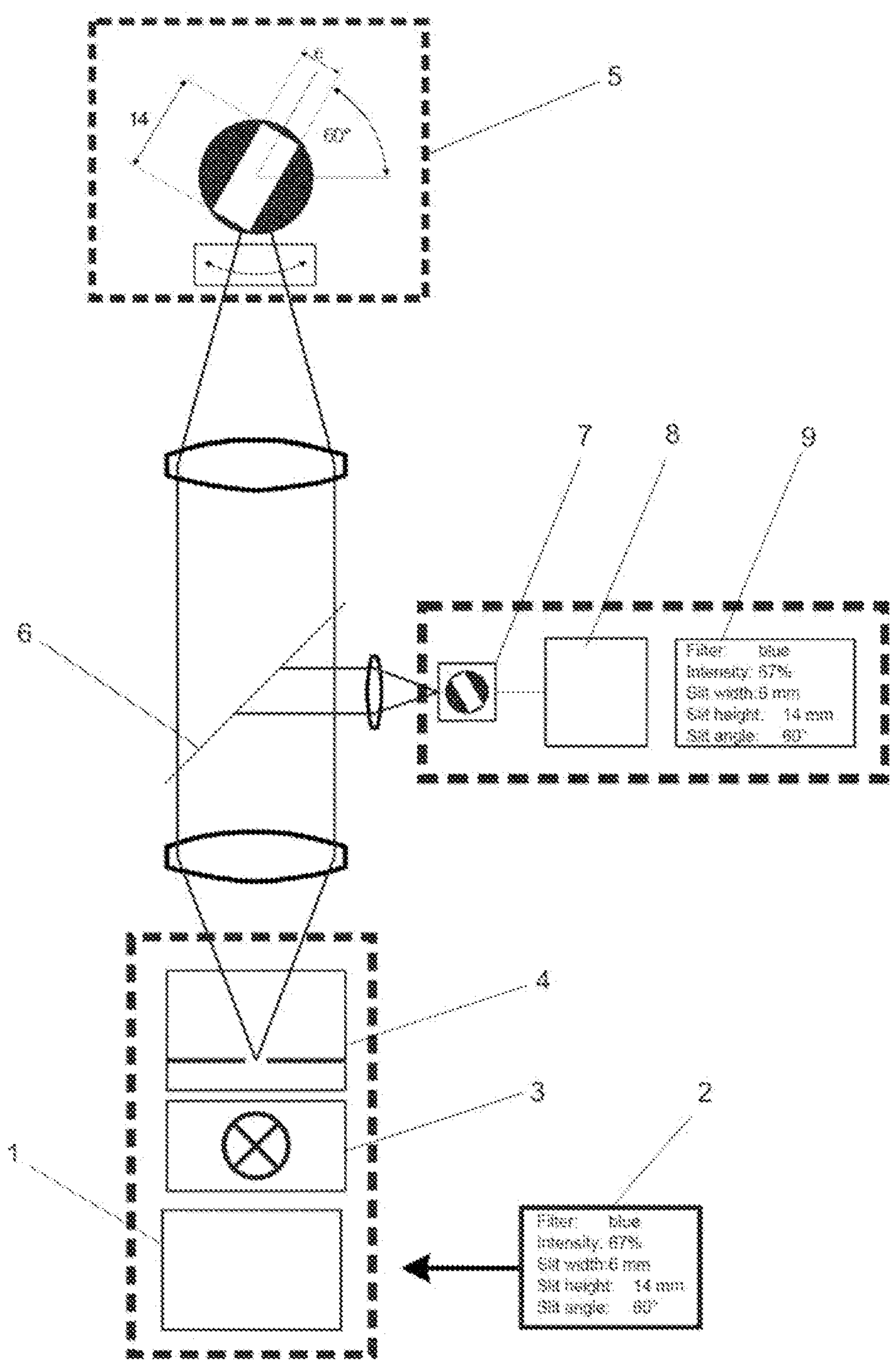
FIG. 2: is a schematic representation of the arrangement according to the invention using the example of a slit lamp.

In this respect, FIG. 2 shows a schematic representation of the arrangement according to the invention using the example of a slit lamp. The illumination parameters 2 desired in exemplary fashion are set on the actuating unit 1 in order to generate the corresponding illumination radiation distribution in the focal plane 5 with the aid of the illumination unit 3 and the slit generating unit 4 (depicted in simplified fashion).

The beam splitter 6 is used to output couple a portion of the illumination radiation, the latter being imaged on the spatially resolving image sensor 7 for the purposes of analyzing the illumination radiation. The microprocessor 8 evaluates the sensor data transmitted from the spatially resolving image sensor 7, combines the said sensor data with any existing calibration data by calculation, thereby determines the real illumination parameters of the illumination radiation and presents the latter on a display 9.

In accordance with a further example embodiment of the arrangement according to the invention, the arrangement comprises an additional sensor element for the polarization-dependent analysis of the output coupled portion of the illumination radiation. This is the only way to be able to detect polarization-dependent properties.

A Stokes setup could be used to this end, for example, within the scope of which at least 4 different polarization states (parallel or serial) are generated and measured, and the polarization state of the radiation is then calculated back from these.

Further embodiments relate to the camera containing the spatially resolving image sensor.

An example embodiment provides for a present camera observing the actual image field to comprise specific algorithms for analyzing and evaluating the illumination information from the overall image.

Furthermore, it would be useful, for example, if a present camera used to record image information comprises specific algorithms for analyzing and evaluating the illumination information from the overall image.

The solution according to the invention provides a method and an arrangement for setting and controlling parameters of the illumination field of ophthalmological devices, with which the disadvantages of the solutions known from the prior art are rectified. The proposed solution makes it possible to set and control a multiplicity of parameters of the illumination and/or observation field of ophthalmological devices and minimize the susceptibility to faults and mutual interference of the sensors in the process.

The fact that the solution can record and analyze a plurality of parameters at the same time using just one sensor is useful. The use of the image sensor of a camera is also useful in that the entire structure can be miniaturized considerably.

The invention claimed is:

1. A method for setting and controlling parameters of an illumination field of ophthalmological devices, the method comprising:

setting desired illumination parameters;

generating illumination radiation with the desired illumination parameters;

converting the illumination radiation into a light distribution in a focal plane;

outputting, coupling and directing a portion of the illumination radiation to a sensor for analysis;

extracting and imaging a portion of the light distribution in the focal plane onto the sensor using a separate lens and a beam splitter;

determining the light distribution in the focal plane by application of a factor selected from a group consisting of slit width, slit height, slit rotation, light color, light intensity and a combination of the foregoing;

determining real illumination parameters of the illumination radiation from data from the sensor; and using a spatially resolving image sensor as the sensor that analyzes an output coupled portion of the illumination radiation.

2. The method as claimed in claim 1, further comprising using a digital camera for the spatially resolving image sensor.

3. The method as claimed in claim 1, further comprising using the following illumination parameters to generate a desired light distribution: brightness, color, light field shape, polarization and a combination of the foregoing.

4. The method as claimed in claim 1, wherein the desired illumination parameters are specified by the system or by the user.

5. The method as claimed in claim 1, wherein the output coupled portion of the radiation reflects the real light distribution and does not change the real light distribution as far as possible.

6. The method as claimed in claim 2, wherein an image sensor of the digital camera records image data continuously or sequentially.

7. The method as claimed in claim 6, further comprising utilizing a dynamic range of the image sensor.

8. The method as claimed in claim 7, further comprising using the dynamic range of the image sensor as a light output detector.

9. The method as claimed in claim 6, further comprising analyzing the images recorded by the image sensor and determining the parameters using adapted algorithms, optimized algorithms or both.

10. The method as claimed in claim 9, further comprising checking validity of the image data recorded by the image sensor in a first step.

11. The method as claimed in claim 1, further comprising using calibration values to determine the parameters.

12. The method as claimed in claim 1, further comprising detecting an illuminated field and edges thereof in image data recorded by the image sensor and determining width, length and orientation of a slit therefrom.

13. The method as claimed in claim 1, further comprising deducing a color of an illuminated field from an intensity of differently colored partial images in image data recorded by the image sensor.

14. The method as claimed in claim 1, further comprising using image processing algorithms to detect whether one or more of the desired parameters are set correctly in the image data recorded by the image sensor.

15. The method as claimed in claim 1, further comprising storing the real illumination parameters of the illumination radiation for documentation purposes, for reproduction purposes or both.

16. The method as claimed in claim 1, further comprising storing the parameters determined from the recorded images and the size of the images as meta-information or using the parameters determined from the recorded images and the size of the images as an input variable for a control loop of the illumination module.

17. The method as claimed in claim 1, further comprising making the real illumination parameters available to the user as a numerical representation, a pictorial representation or both.

18. The method as claimed in claim 17, further comprising presenting the numerical and/or pictorial representations of the real illumination parameters on a display or coupled into an observation beam path.

* * * * *